US00PP35564P2

(12) United States Plant Patent
Michael

(10) Patent No.: US PP35,564 P2
(45) Date of Patent: Dec. 26, 2023

(54) XSEMPONIUM PLANT NAMED 'DIAMOND'

(50) Latin Name: *xSemponium*
Varietal Denomination: Diamond

(71) Applicant: Surreal Succulents, Marazion (GB)

(72) Inventor: Daniel Michael, Marazion (GB)

(73) Assignee: SURREAL SUCCULENTS, Marazion (GB)

( * ) Notice: Subject to any disclaimer, the term of this patent is extended or adjusted under 35 U.S.C. 154(b) by 0 days.

(21) Appl. No.: 18/127,999

(22) Filed: Mar. 29, 2023

(51) Int. Cl.
*A01H 6/00* (2018.01)
*A01H 5/02* (2018.01)

(52) U.S. Cl.
USPC ..... Plt./373

(58) Field of Classification Search
USPC ..... Plt./373
CPC ..... A01H 6/00; A01H 5/02
See application file for complete search history.

*Primary Examiner* — Keith O. Robinson
(74) *Attorney, Agent, or Firm* — Penny J Aguirre

(57) ABSTRACT

A new cultivar of x*Semponium* plant named 'Diamond' that characterized by its compact, dense growth habit with short stems, its uniformly neat, conical growth habit, its large, strong rosettes with leaves that are spathulate-shaped and mucronate pointed tips, its showy flower heads that are firm and yellow in color, and its unique foliage coloration that is bright lime green with red margins (with sun exposure).

2 Drawing Sheets

Botanical classification: x*Semponium.*
Variety denomination: 'Diamond'.

CROSS REFERENCE TO RELATED APPLICATIONS

This application claims priority to European Community Plant Variety Office (CPVO) Plant Breeder's Rights Application No. 2022/2866 filed on Dec. 7, 2022, under 35 U.S.C. 119(f), the entire contents of which is incorporated by reference herein. This application is also related to a Plant Breeders' Rights application in The United Kingdom filed on Dec. 21, 2022, Application No. 254-3, a U.S. Plant Patent for a plant derived from the same breeding program that is entitled x*Semponium* Plant Named 'Sienna' (U.S. Plant Pat. No. 34,201) and a U.S. Plant Patent Application filed for a plant derived from the same breeding program that is entitled x*Semponium* Plant Named 'Destiny' (U.S. Plant patent application Ser. No.18/110,002).

BACKGROUND OF THE INVENTION

The present invention relates to a new and distinct cultivar of x*Semponium*, an interspecific hybrid and referred to hereinafter by its cultivar name, 'Diamond'. The new cultivar of x*Semponium* is a frost hardy succulent subshrub perennial grown for ornamental foliage use in landscapes and containers.

The new cultivar arose from an ongoing breeding program by the Inventor in Penzance, Cornwall, United Kingdom. The goal of the breeding program was to produce a new cultivar of x*Semponium* with unique foliage coloration, a compact growth habit, a low growing dense and neat plant habit, and large rosettes.

The new cultivar arose from a cross made by the Inventor in 2015 between *Aeonium* 'Ice Warrior' (not patented) as the female parent and *Sempervivum ciliosum* 'Green Ice' (not patented) as the male parent. The Inventor selected 'Diamond' as a single unique plant amongst the seedlings that resulted from the above cross in 2016.

Asexual propagation of the new cultivar was first accomplished by the Inventor by stem root cuttings in 2016 in Penzance, Cornwall, United Kingdom. Asexual propagation by stem root cuttings and offshoots has determined the characteristics to be stable and reproduced true to type in successive generations.

SUMMARY OF THE INVENTION

The following traits have been repeatedly observed and are determined to be the characteristics of the new cultivar. These attributes in combination distinguish 'Diamond' as a unique cultivar of x*Semponium.*

1. 'Diamond' exhibits a compact, dense growth habit with short stems.
2. 'Diamond' exhibits a uniformly neat, conical growth habit.
3. 'Diamond' exhibits large, strong rosettes with leaves that are spathulate-shaped and mucronate pointed tips.
4. 'Diamond' exhibits showy flower heads that are firm and yellow in color.
5. 'Diamond' exhibits unique foliage coloration that is bright lime green with red margins (with sun exposure).

The female parent plant differs from 'Diamond' in having taller stems, fewer leaves per rosette, a plant habit that is less dense and compact, leaves that are broader in size with less pointed tips, foliage that is green with margins that are dusty purple in color and inflorescences that are less robust, less firm, and less open in stature. The male parent plant differs from 'Diamond' in having foliage that is green in color with no red margins, a smaller plant size, a less robust and flatter plant habit. 'Diamond' can be most closely compared to the x*Semponium* cultivars 'Destiny' and 'Sienna'. 'Destiny' is similar to 'Diamond' in having a low growing habit and large sized rosettes. 'Destiny' differs from 'Diamond' in having leaves that are broader and larger in size with less pointed tips, foliage that is dark green and purple in color with veiny markings, and rosettes that are larger in size. 'Sienna' is similar to 'Diamond' in having a low growing habit. 'Sienna' differs from 'Diamond' in having leaves that are longer and broader in size with less pointed tips, a greater production of offsets, and foliage that is solid in color (no colored margins) and changes throughout the year.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Surreal Succulents, Royal Horticulture Society, YouTube, Thompson & Morgan, Visions Pictures, Van Meuwen, Dobies, Suttons, Twitter, Facebook, House Beautiful, Amazon, Flipkart, Tumblr, Plantipp, Cowell's Garden Centre, Instagram, Yahoo, Floral Daily, Gardens Illustrated, Exotic Plants, Gardening Express, Horticulture Week, Mandy Can U Dig It, Listen Notes, Cactus and Succulent Review, Pro Landscape Magazine, Press Reader, Matteoragni, bloom in business, cactus mania, Gabot, Falmouth Packet, Gartenpraxis, katakunabloom, sohu, Friedrich Strauss, floraviva, The International Crassulaceae Network, floraxchange, Beyond the Garden Gates, varb, and tumpik.

BRIEF DESCRIPTION OF THE DRAWINGS

The accompanying color photographs illustrate the overall appearance and distinct characteristics of the new cultivar.

The photograph in FIG. 1 was taken of a plant 3 months in age as grown in a greenhouse in a 17-cm container in Waddinxveen, The Netherlands and provides a close-up view of a rosette of 'Diamond' in fall.

Figure 1:
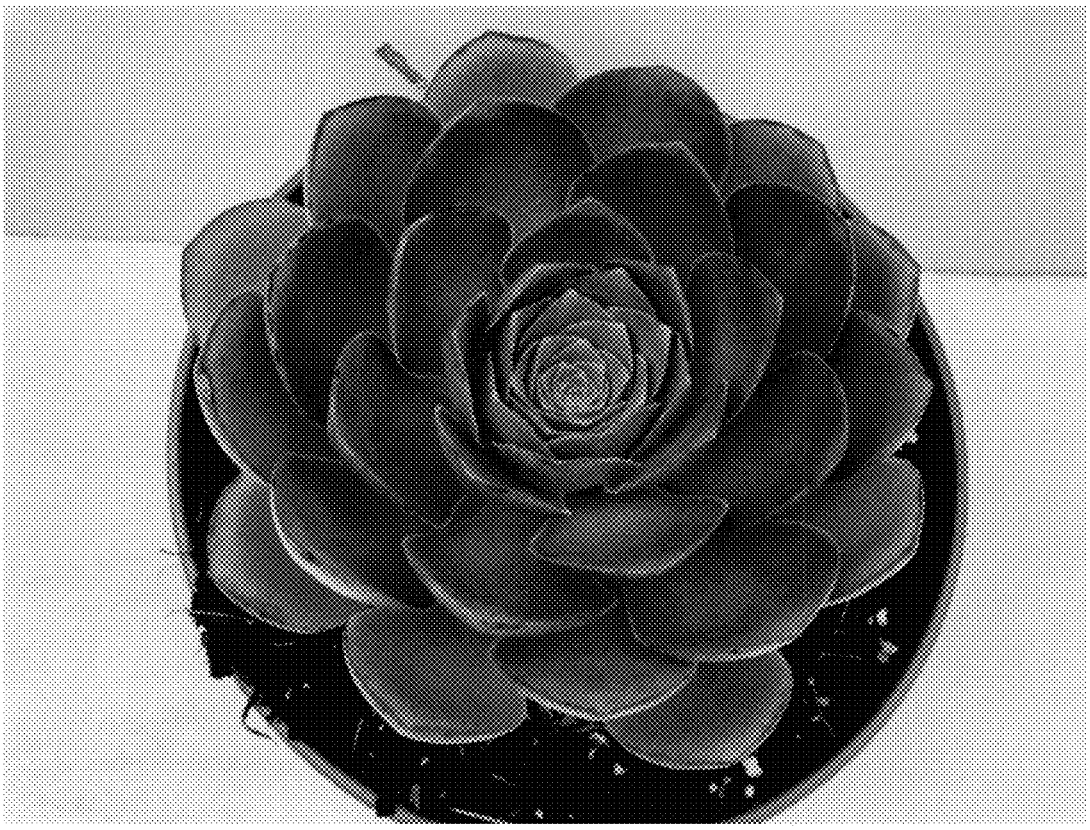
Figure 2:
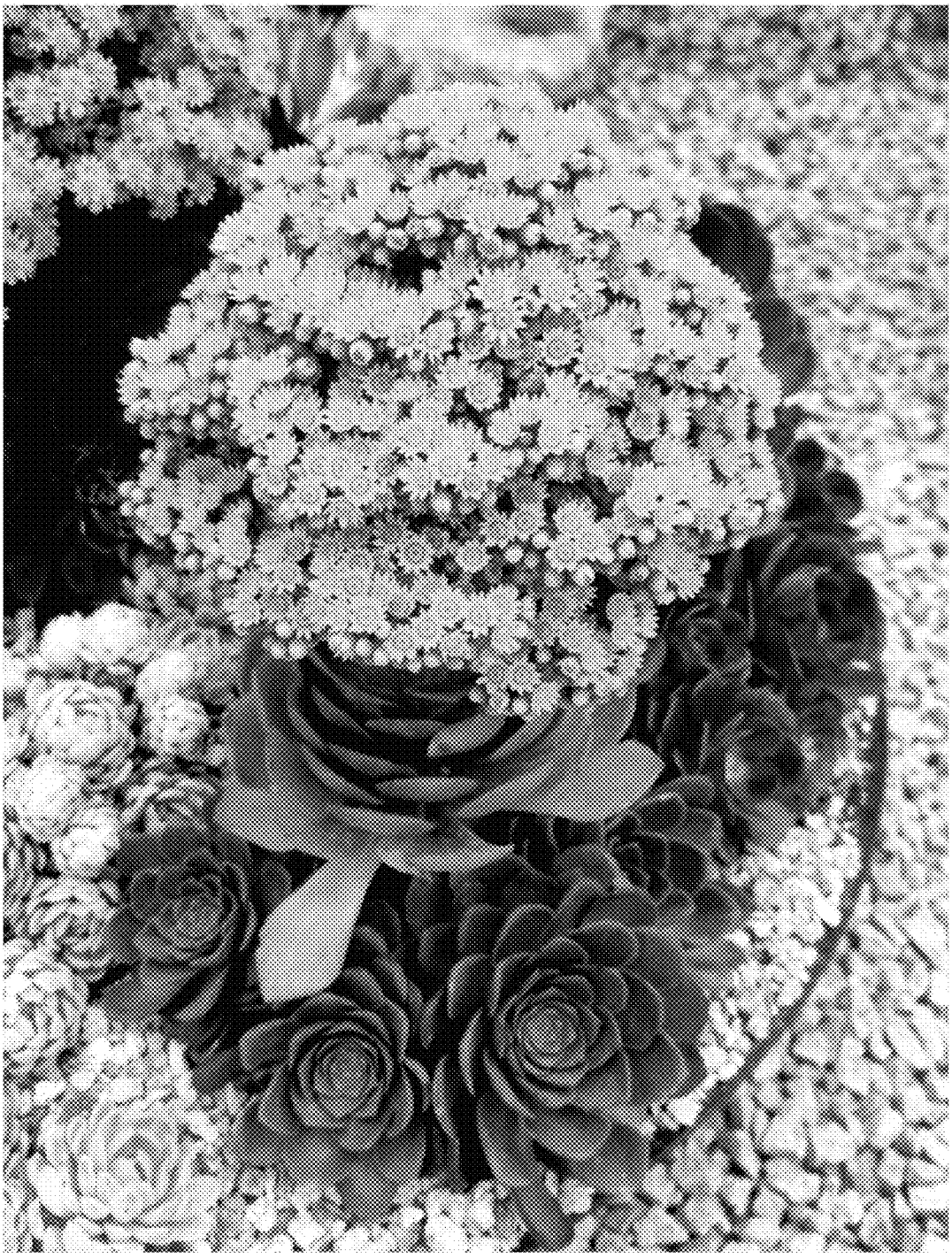

The photograph in FIG. 2 was taken of a 3-year-old plant of 'Diamond' as planted from a 5-liter container in Penzance, Cornwall, United Kingdom and provides a view of 'Diamond' in bloom.

The colors in the photographs may differ slightly from the color values cited in the detailed botanical description, which accurately describe the colors of the new x*Semponium*.

DETAILED BOTANICAL DESCRIPTION

The following is a detailed description of the new cultivar as observed on 18-month-old plants of 'Diamond' as grown in a greenhouse in 17-cm containers in Waddinxveen, The Netherlands with flowering data taken from 3-year-old plants as grown outdoors (April to October) and in an unheated polytunnel (November to March) in 5-liter containers in Penzance, Cornwall, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen succulent perennial.

*Blooming period*.—May through July in the United Kingdom.

*Plant shape*.—Conical.

*Plant habit*.—Compact, dense basal rosette with offsets clustered around main rosette.

*Height and spread*.—Reaches up to 30 cm in height and width as a mature plant.

*Hardiness*.—At least hardy to −5° C., has not been tested in colder climates.

*Diseases and pests*.—No susceptibility or resistance to diseases or pests has been observed.

*Root description*.—Fibrous.

*Propagation*.—Stem cuttings.

*Root development*.—Roots initiate in an average of 6 weeks and fully root as a young plant in a P7 container in about 2 months.

*Growth rate*.—Moderate.

Stem description:

*Stem shape*.—Cylindrical.

*Stem size*.—1.8 cm in width and up to 1 cm in length.

*Stem surface*.—Smooth with leaf scars.

*Stem arrangement*.—Only 1 main stem.

*Stem aspect*.—Vertical.

*Internode length*.—Not applicable.

*Stem color*.—145C, scars 199A.

Foliage description:

*Leaf shape*.—Spathulate.

*Leaf division*.—Simple.

*Leaf arrangement*.—Rosette.

*Leaf quantity*.—Average of 67 per rosette.

*Leaf base*.—Narrowly cuneate.

*Leaf apex*.—Round, mucronate.

*Leaf venation*.—No veins visible.

*Leaf margins*.—Ciliate.

*Leaf attachment*.—Sessile.

*Leaf orientation*.—Flat to slightly concave, held in an upward position.

*Leaf substance*.—Succulent.

*Leaf surface*.—Both surfaces smooth and glossy.

*Leaf color*.—Young leaves; upper surface; tip 137A, center 137B, base 145A, lower surface 137D, base 145A, when mature develops margins on the upper portion of the upper and lower surfaces 60B in color (with sun exposure).

*Leaf size*.—Average of 9 cm in length and 1 cm in width.

*Rosette size*.—Average of 7 cm in height and 17 cm in width.

Flower description:

*Inflorescence type*.—Dense, terminal cymes.

*Inflorescence size*.—20 cm in diameter, 15 cm in depth.

*Lastingness of inflorescence*.—6 to 8 weeks.

*Flower type*.—Perfect, spreading.

*Flower number*.—800 flowers per branched cyme.

*Flower fragrance*.—None.

*Flower buds*.—Oval in shape, about 6 mm length and 5 mm in diameter, slightly pubescent, color; 145A, 145B and 145C.

*Flower size*.—About 1 cm in depth and 1.5 cm in diameter.

*Peduncles*.—Strong, round in shape, 145A in color, slightly pubescent surface, primary; 10 cm in length and 2.5 cm in diameter, secondary; 4 cm in length and 1 cm in diameter.

*Pedicels*.—Strong, round in shape, 1 cm in length and 3 mm in diameter, 145A in color, slightly pubescent surface.

*Sepals*.—10 to 12, 3.5 mm in length and 1 mm in width, both surfaces 145A in color, entire margins, acute apex, truncate base, pubescent on both surfaces.

*Petals*.—10 to 12, 4.5 mm in length, 2 mm in width, lanceolate in shape, truncate base, acute apex, entire margin, color of inner and outer surfaces when opening and fully open; 1B, glabrous on both surfaces.

Reproductive organs:

*Pistils*.—12, stigma; 1 mm in length and 1B in color, style; 3 mm in length and 1B in color, ovary; small, single celled and translucent in color.

*Stamens*.—20, filament; 5 mm in length, 1B in color, anther; 1 mm in length and 1A in color, pollen is moderate in quantity.

*Fruit*.—Fruit and seed production has not been observed.

It is claimed:

1. A new and distinct variety of x*Semponium* plant named 'Diamond' as described and illustrated herein.

* * * * *